(12) United States Patent
Deliwala (10) Patent No.: US 9,304,202 B2
(45) Date of Patent: Apr. 5, 2016

(54) MULTIUSE OPTICAL SENSOR

(75) Inventor: Shrenik Deliwala, Andover, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 1033 days.

(21) Appl. No.: 12/783,673

(22) Filed: May 20, 2010

(65) Prior Publication Data

US 2010/0305418 A1  Dec. 2, 2010

Related U.S. Application Data

(60) Provisional application No. 61/181,538, filed on May 27, 2009, provisional application No. 61/264,919, filed on Nov. 30, 2009.

(51) Int. Cl.
| | |
|---|---|
| *A61B 5/00* | (2006.01) |
| *G01S 17/06* | (2006.01) |
| *A61B 5/1455* | (2006.01) |
| *G01S 3/783* | (2006.01) |
| *G01S 5/16* | (2006.01) |
| *G01S 17/87* | (2006.01) |
| *A61B 5/024* | (2006.01) |

(52) U.S. Cl.
CPC .............. *G01S 17/06* (2013.01); *A61B 5/14551* (2013.01); *A61B 5/721* (2013.01); *G01S 3/783* (2013.01); *G01S 5/16* (2013.01); *G01S 17/87* (2013.01); *A61B 5/02427* (2013.01)

(58) Field of Classification Search
CPC ........ G03B 13/18; G03B 13/20; G03B 13/22; A61B 5/00
USPC .................................................. 600/324, 310
See application file for complete search history.

(56) References Cited

U.S. PATENT DOCUMENTS

| 4,441,810 A | 4/1984 | Momose et al. |
|---|---|---|
| 4,688,933 A | 8/1987 | Lapeyre |

(Continued)

FOREIGN PATENT DOCUMENTS

| CN | 1989895 A | 7/2007 |
|---|---|---|
| EP | 0271340 A1 | 6/1988 |

(Continued)

OTHER PUBLICATIONS

PCT International Search Report and Written Opinion mailed on Jul. 26, 2010, for PCT/US2010/035604.

(Continued)

*Primary Examiner* — Clayton E LaBalle
*Assistant Examiner* — Fang-Chi Chang
(74) *Attorney, Agent, or Firm* — Kenyon & Kenyon, LLP (57) ABSTRACT

One or more electromagnetic radiation sources, such as a light emitting diode, may emit electromagnetic waves into a volume of space. When an object enters the volume of space, the electromagnetic waves may reflect off the object and strike one or more position sensitive detectors after passing through an imaging optical system such as glass, plastic lens, or a pinhole located at known distances from the sources. Mixed signal electronics may process detected signals at the position sensitive detectors to calculate position information as well as total reflected light intensity, which may be used in medical and other applications. A transparent barrier may separate the sources and detectors from the objects entering the volume of space and reflecting emitted waves. Methods and devices are provided.

40 Claims, 10 Drawing Sheets

(56) References Cited

U.S. PATENT DOCUMENTS

| | | | |
|---|---|---|---|
| 4,956,546 A | 9/1990 | Nishibe et al. | |
| 4,999,483 A | 3/1991 | Okamoto | |
| 5,187,540 A | 2/1993 | Morrison | |
| 5,196,689 A | 3/1993 | Sugita et al. | |
| 5,264,910 A | 11/1993 | Hill | |
| 5,305,091 A | 4/1994 | Gelbart et al. | |
| 5,361,117 A | 11/1994 | Nonaka | |
| 5,367,373 A | 11/1994 | Busch-Vishniac et al. | |
| 5,422,693 A | 6/1995 | Vogely et al. | |
| 5,483,060 A | 1/1996 | Sugiura et al. | |
| 5,527,822 A * | 6/1996 | Scheiner | 514/465 |
| 5,574,479 A | 11/1996 | Odell | |
| 5,598,187 A | 1/1997 | Ide et al. | |
| 5,604,695 A | 2/1997 | Cantin et al. | |
| 5,627,565 A | 5/1997 | Morishita et al. | |
| 5,644,126 A | 7/1997 | Ogawa | |
| 5,644,385 A | 7/1997 | Mizuno | |
| 5,719,670 A | 2/1998 | Duboz et al. | |
| 5,793,353 A | 8/1998 | Wu | |
| 5,796,387 A | 8/1998 | Curran et al. | |
| 5,825,481 A | 10/1998 | Alofs et al. | |
| 5,892,501 A | 4/1999 | Kim et al. | |
| 5,900,863 A | 5/1999 | Numazaki | |
| 5,909,296 A | 6/1999 | Tsacoyeanes | |
| 5,974,365 A | 10/1999 | Mitchell | |
| 6,014,129 A | 1/2000 | Umeda et al. | |
| 6,026,313 A * | 2/2000 | Kexin | 600/310 |
| 6,130,663 A | 10/2000 | Null | |
| 6,181,877 B1 | 1/2001 | Yoshida | |
| 6,274,862 B1 | 8/2001 | Rieger | |
| 6,280,327 B1 | 8/2001 | Leifer et al. | |
| 6,330,064 B1 | 12/2001 | Rieder | |
| 6,343,171 B1 | 1/2002 | Yoshimura et al. | |
| 6,473,189 B1 | 10/2002 | Reedy | |
| 6,495,833 B1 | 12/2002 | Alfano et al. | |
| 6,498,860 B1 | 12/2002 | Sasaki et al. | |
| 6,521,882 B1 | 2/2003 | Sumiya et al. | |
| 6,529,281 B2 | 3/2003 | Takeshita et al. | |
| 6,567,071 B1 | 5/2003 | Curran et al. | |
| 6,597,443 B2 | 7/2003 | Boman | |
| 6,997,879 B1 * | 2/2006 | Turcott | 600/507 |
| 7,012,691 B2 | 3/2006 | Sugiyama et al. | |
| 7,158,659 B2 | 1/2007 | Baharav et al. | |
| 7,352,477 B2 | 4/2008 | Seo | |
| 7,461,543 B2 | 12/2008 | Degertekin | |
| 7,473,884 B2 | 1/2009 | Fouquet et al. | |
| 7,505,033 B2 | 3/2009 | Guo et al. | |
| 7,655,937 B2 | 2/2010 | Hotelling et al. | |
| 7,737,409 B2 | 6/2010 | Deliwala et al. | |
| 7,787,122 B2 | 8/2010 | Saito et al. | |
| 7,852,317 B2 | 12/2010 | Grunnet-Jepsen et al. | |
| 7,931,535 B2 | 4/2011 | Ikeda et al. | |
| 7,944,551 B2 | 5/2011 | Addison et al. | |
| 7,978,311 B2 | 7/2011 | Deliwala | |
| 8,022,928 B2 | 9/2011 | Ye | |
| 8,133,769 B1 | 3/2012 | Tivarus | |
| 8,310,656 B2 | 11/2012 | Zalewski | |
| 2001/0043337 A1 | 11/2001 | Takeshita et al. | |
| 2002/0053635 A1 | 5/2002 | Schroter et al. | |
| 2003/0090650 A1 | 5/2003 | Fujieda | |
| 2003/0223085 A1 | 12/2003 | Rekimoto | |
| 2004/0135825 A1 | 7/2004 | Brosnan | |
| 2004/0222969 A1 | 11/2004 | Buchenrieder | |
| 2004/0225207 A1 | 11/2004 | Bae et al. | |
| 2004/0266528 A1 | 12/2004 | Wang | |
| 2005/0259097 A1 | 11/2005 | Lehoty et al. | |
| 2007/0018970 A1 | 1/2007 | Tabasso et al. | |
| 2007/0078311 A1 | 4/2007 | Al-Ali et al. | |
| 2007/0103698 A1 | 5/2007 | Liu et al. | |
| 2007/0138377 A1 | 6/2007 | Zarem | |
| 2007/0165225 A1 | 7/2007 | Trainer | |
| 2007/0252821 A1 * | 11/2007 | Hollemans et al. | 345/173 |
| 2007/0265075 A1 | 11/2007 | Zalewski | |
| 2008/0009690 A1 * | 1/2008 | Debreczeny et al. | 600/336 |
| 2008/0013826 A1 | 1/2008 | Hillis et al. | |
| 2008/0089587 A1 | 4/2008 | Kim et al. | |
| 2008/0100825 A1 | 5/2008 | Zalewski | |
| 2008/0150898 A1 | 6/2008 | Low et al. | |
| 2008/0215974 A1 | 9/2008 | Harrison et al. | |
| 2008/0220814 A1 * | 9/2008 | Hedtke et al. | 455/556.1 |
| 2008/0221418 A1 | 9/2008 | Al-Ali et al. | |
| 2008/0278445 A1 | 11/2008 | Sweetser et al. | |
| 2009/0062667 A1 | 3/2009 | Fayram et al. | |
| 2009/0078858 A1 | 3/2009 | Fouquet et al. | |
| 2009/0085869 A1 | 4/2009 | Destura et al. | |
| 2009/0091532 A1 | 4/2009 | Hockett | |
| 2009/0092284 A1 | 4/2009 | Breed et al. | |
| 2009/0280843 A1 * | 11/2009 | Wisebourt et al. | 455/466 |
| 2009/0325408 A1 * | 12/2009 | Wong et al. | 439/135 |
| 2010/0231513 A1 | 9/2010 | Deliwala | |
| 2010/0271617 A1 * | 10/2010 | Damink et al. | 356/5.09 |
| 2010/0277431 A1 * | 11/2010 | Klinghult | 345/174 |
| 2010/0305418 A1 | 12/2010 | Deliwala | |
| 2010/0309457 A1 | 12/2010 | Cui et al. | |
| 2012/0280107 A1 | 11/2012 | Skurnik et al. | |

FOREIGN PATENT DOCUMENTS

| | | |
|---|---|---|
| EP | 0905646 A1 | 3/1999 |
| WO | 00/07148 | 2/2000 |

OTHER PUBLICATIONS

Amann, Markus-Christian, Thierry Bosch, Marc Lescrure, Risto Myllyla, Marc Rioux, "Laser ranging: a critical review of usual techniques for distance measurement", Optical Engineering, vol. 40, No. 1, Jan. 2001, pp 10-19.

International Search Report dated Jul. 27, 2010, in counterpart international application No. PCT/US2010/036438, 9 pages.

International Search Report dated Aug. 5, 2009, in counterpart international application No. PCT/US2009/041539, 12 pages.

Supplementary EP Search Report issued in EP Application No. 10781228, dated Jul. 31, 2014, 9 pages.

EP Communication including Supplementary European Search Report issued in EP Appln. No. 10781029.3, dated Jun. 27, 2014, 6 pages.

\* cited by examiner

MULTIUSE OPTICAL SENSOR

CROSS-REFERENCE TO RELATED APPLICATIONS

This application claims priority under 35 U.S.C. §119 to provisional application 61/181,538, filed May 27, 2009, and entitled "APPLICATIONS FOR POSITION MEASUREMENT SYSTEMS USING POSITION SENSITIVE DETECTORS" and to provisional application 61/264,919, filed Nov. 30, 2009 and entitled "MULTIUSE OPTICAL SENSOR." Both of these provisional applications are incorporated herein by reference in their entireties.

BACKGROUND

Optical sensing technology has been used to locate and track movement of objects in two and three dimensions. U.S. patent application Ser. No. 12/327,511, filed Dec. 3, 2008, and entitled "Method of Location an Object in 3D" and U.S. patent application Ser. No. 12/435,499, filed May 5, 2009, and entitled "Optical Distance Measurement by Triangulation of an Active Transponder" provide examples and details regarding how optical sensing technology may be used to locate and track objects. The contents of both these patent applications are incorporated by reference herein.

Some optical systems locate and track objects by placing one or more light sources in a first object and one or more position sensitive light detectors in a second object. The location of the first object relative to the second object may then be calculated using triangulation or other mathematical calculations based on the detected position of light from the light source(s) directly striking the detector(s). These optical systems may be limited to tracking objects equipped with either a complementary light source or detector. Existing medical devices such as optical heart rate monitors and blood oxygen level measurement devices use a light source, light detector, and simple photodetector geometry to calculate heart rates or measure blood oxygen levels.

These existing optical pulse oximeters and heart rate monitors work by having a user place a transparent body part, such as a fingertip or earlobe between the light sources and detector(s). As the arterial blood vessels expand and contract with each heartbeat, the amount of light flowing through the body part changes. A user's heartbeat can be measured based on the change in light detected at the detector. Different colors of light are used to measure blood oxygen level since absorbance of oxygenated and deoxygenated blood varies at different colors. In blood oxygen monitors, "locking" measurements to the heartbeat signal may allow some rejection of interference signals from stagnant blood outside the arteries.

In order for these existing pulse oximeters and heart rate monitors to provide reliable results, manufacturers have placed the light sources and detectors flush or close to the transparent body part. This was done to prevent ambient light from reaching the detector, which caused signal interference and inaccurate results. Light sources and detectors were often placed close the body part by a mechanical device, such as a clip or spring, which also requires additional maintenance. Manufacturers have also tried to reducing the effects of other sources of error leading to inaccurate results, such as movements of the body part during heart rate/photoplethysmograph (PPG) and oximetry measurements, by implementing various algorithms to "guess" and reduce errors caused by body part movements.

Another optical object location and tracking technique is used in some optical mice. In this traditional technique, light is emitted from a light source in the bottom of the object, in this case a computer mouse; reflected off the surface of another object, such as desktop or mouse pad; and detected by a relatively small pixel count CMOS camera whose output when coupled with optical flow algorithm produces accurate velocity measurement. This existing technique, however, is sensitive to interference from ambient light and cannot be used in environments where interfering light from outside sources can reach the detector.

There is a need for an optical position and movement tracking device that can track objects unequipped with a complementary light source or detector without being affected by interference from ambient light. This need applies to both optical mouse applications as well as to measurements of medical information, such as PPG. There is also a need to integrate position tracking information with the medical measurements so that movement errors from body part movements can be directly removed from PPG data instead of through "guessing" algorithms. There is also a need to use position measurement information to guide a user in repositioning their body part to an optimal location for measurement. There is also need for performing each of these functions in a "reflection mode" where light emitted from a source is reflected off the object or body part and detected at a detector in order to avoid mechanical design and maintenance issues associated with placing an object between a light source and detector or affixing a light source or detector to the object.

DETAILED DESCRIPTION

Embodiments of the invention enable measurement of proximity, motion, and medical diagnostic functions from light reflected off a body part, and may be incorporated in compact, handheld devices. In an embodiment of the invention, one or more sources of electromagnetic radiation, also referred to interchangeably as light, such as a light emitting diode, may emit electromagnetic waves into a volume of space. When an object in an embodiment enters the volume of space, the electromagnetic waves may reflect off the object and strike one or more position sensitive detectors after passing through imaging optics. Imaging optics may include a glass, plastic, or pinhole lens located at known distances from the sources and/or detectors. A transparent barrier may separate the sources and detectors from the objects entering the volume of space and reflecting emitted waves. Mixed signal electronics may process detected signals at the position sensitive detectors to calculate a position of the object as well as an intensity of the light reflected by the object. The object may be anything capable of reflecting light, including for example, a finger, body, tree, and vehicle.

The calculations may measure the position of the object and reflected intensity of light as the object is moved both along the transparent barrier and in the volume of space around the transparent barrier. The electronics may also be used to calculate additional information from the position and/or reflected intensity results including a proximity of the object to the detector; a pressure applied by an elastic object to the surface of the transparent barrier; and medical information including a heart rate, photoplethysmograph (PPG), or blood oxygen content, if the object is a body part. In an embodiment, the sources and position sensitive detectors may be modulated in the time or frequency domain to prevent interference from ambient electromagnetic radiation and distinguish between signals from different light sources.

Embodiments of the invention include a single device and a signal chain capable of multiple modalities. Position information of objects moving in the "air", along the surface of a barrier, or both may be tracked, and the proximity of the object to a location, such as the surface of the barrier may be calculated. Other medical information, such as heart rate, PPG, and blood oxygen content may also be calculated.

Locating a Light Spot on a One-Dimensional Optical Detector

Figure 1:
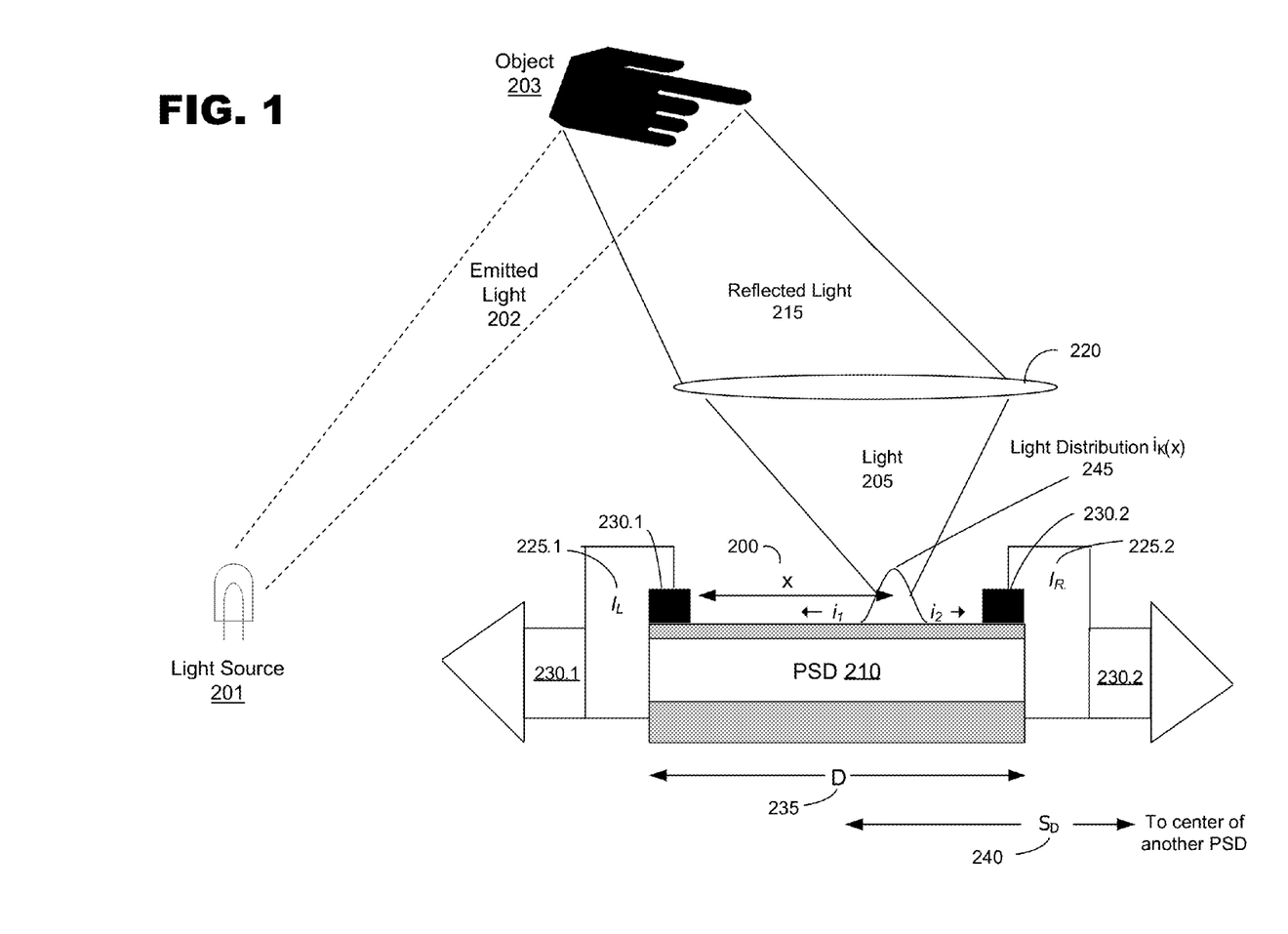
FIG. 1 shows a method for measuring the location of focused light on a one-dimensional position sensitive device.

FIG. 1 illustrates measuring the location x 200 of focused light 245 on a linear position sensitive detector (PSD) 210. Light 202 emitted from a light source 201 may strike object 203, reflect 215 off the object, and pass through a focusing lens or aperture 220. After passing through the lens 220, the focused light 205 may fall on the PSD 210 with light distribution 245. The reflected light 215 may be modeled as if it were a light spot incident on the PSD 210. The light distribution 245 may generate lateral currents $i_1$ and $i_2$ in the PSD 210 and currents $I_L$ 225.1 and $I_R$ 225.2 at respective electrical contacts 230.1, 230.2, which are provided at opposite ends of the linear PSD 210. The lateral currents $i_1$ and $i_2$ may be proportionate to the reflected light 215. The currents $I_L$ 225.1 and $I_R$ 225.2 may be amplified by respective amplifiers 230.1, 230.2 and may be digitized for further processing by the electronics (not shown).

The incident light may be modeled as if it were a light spot incident on the PSD 210. The PSD has a length D 235. The electronics may calculate the location x 200 of the spot by applying the following equation:

$$x = \left(\frac{I_L - I_R}{I_L + I_R}\right)\frac{D}{2} \equiv \left(\frac{I_L - I_R}{I_T}\right)\frac{D}{2}$$

In this case, the electronics may calculate x 200 from the center of the detector 210. Note that this follows from the fact that the total photocurrent generated may be distributed among the two contacts 230.1, 230.2 according to the resistance of the PSD 210 surface material. The PSD 210 may be at distance $S_D$ 240 from the center of another PSD (not illustrated).

Locating a Light Spot on a Two-Dimensional Optical Detector

Figure 2:
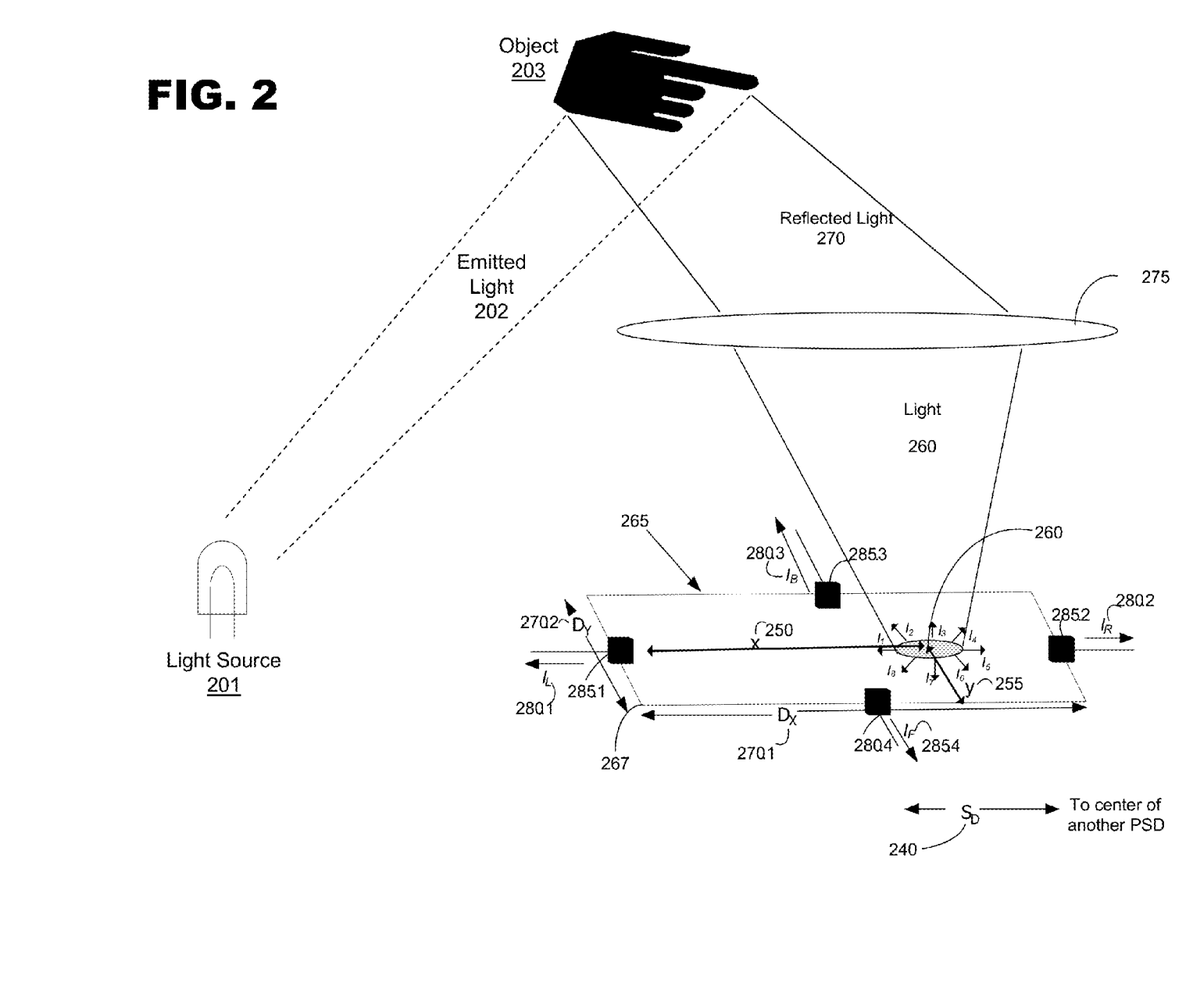
FIG. 2 shows a method for measuring the location of focused light on a two-dimensional position sensitive device.

FIG. 2 illustrates measuring the locations x 250 and y 255 of focused light 260 on a two-dimensional PSD 265. Just as in the previous example, light 202 emitted from a light source 201 may strike object 203, reflect 270 off the object, and pass through a focusing lens or aperture 275. The reflected light 270 may pass through the lens 275, and becomes focused light 260 that falls on the PSD 265 with light distribution 260 that generates lateral currents $i_1 \ldots i_9$ and currents $I_L$ 280.1, $I_R$ 280.2, $I_B$ 280.3, and $I_F$ 280.4 at respective electrical contacts, 285.1, 285.2, 285.3, and 285.4. The currents $I_L$ 280.1, $I_R$ 280.2, $I_B$ 280.3, and $I_F$ 280.4 may be amplified by amplifiers (not illustrated) and may be digitized for further processing by additional electronics (not illustrated).

The incident light may be modeled as if it were a light spot incident on the PSD 265. The PSD 265 has a length of $D_X$ 270.1 and $D_Y$ 270.2. The electronics may calculate the location of x 250 and y 255 of the centroid of the spot 260 by applying the following equations:

$$y = \frac{D_y}{2}\left(\frac{I_F - I_B}{I_F + I_B}\right)$$

$$x = \frac{D_x}{2}\left(\frac{I_L - I_R}{I_L + I_R}\right)$$

In this case, the electronics may calculate x 250 and y 255 from the center of the detector 265. In embodiments, the electronics may calculate adjustments to x 250 and y 255 to adjust for the position of the contacts 285. For example, in an embodiment the contacts 285 may be on the edges of the PSD 265. The electronics may then use equations from coordinate geometry to adjust the values for x 250 and y 255 to adjust for the contacts 285 being located on the edges of the PSD 265. In embodiments, the electronics may calculate adjustments to x 250 and y 255 to adjust for the properties of the PSD 265. Note that this follows from the fact that the total photocurrent generated is distributed among the four contacts 285.1, 285.2, 285.3, and 285.4 according to the resistance of the PSD 265 surface material. The PSD 265 may be $S_D$ 240 from the center of another PSD (not illustrated).

Multiple Light Sources May be Tracked by Using Frequency or Time Modulation

The electronics may calculate the position of multiple light sources using time modulation. For example, each light source may be turned on-off in a predetermined sequence such that only one of the light sources is on at any given time. In this embodiment, only the coordinate corresponding to a particular light source may be measured during a prescribed time interval. Thus, the electronics may calculate positional data for all of the light sources on a time sharing basis. In an embodiment, the light sources may be pulsed and individual light sources given a window in time when each one is pulsed. The electronics may then calculate the centroid of each of light source for each window of time.

Alternatively, the electronics may distinguish between the light sources using frequency domain. For example, the light sources may be modulated at unique frequencies $f_k$. The currents $I_L$ and $I_R$ generated by the optical detectors in response to receiving incident light from the light sources may include frequency components characterized by these modulations, such as:

$$I_L(t) = \sum_{k=sources} \int i_{lk}(x)\cos[2\pi f_k t]x\,dx$$

$$I_R(t) = \sum_{k=sources} \int i_{rk}(D-x)\cos[2\pi f_k t](D-x)\,dx$$

In the above equation, $i_k(x)$ represent the individual spot size distributions from each of the remote light sources on the surface of the optical detectors. The electronics may use these equations to demodulate the left and the right currents $I_L$ and $I_R$ corresponding to each $i_k(x)$ at each of the frequencies $f_k$. Demodulating the currents at each frequency may differentiate light spots on the PSD's surface having different frequencies. The electronics may then calculate the positions of the light sources using the aforementioned equations applied to each of the individual demodulated currents $i_{kL}(x)$ and $i_{kR}(x)$. Thus the electronics may calculate the location of multiple modulated light sources. Furthermore, by repeatedly calculating the location of multiple light sources, the electronics may track changes in the locations of the multiple light sources.

Calculating the Position of X, Y, and Z Coordinates

Figure 3:
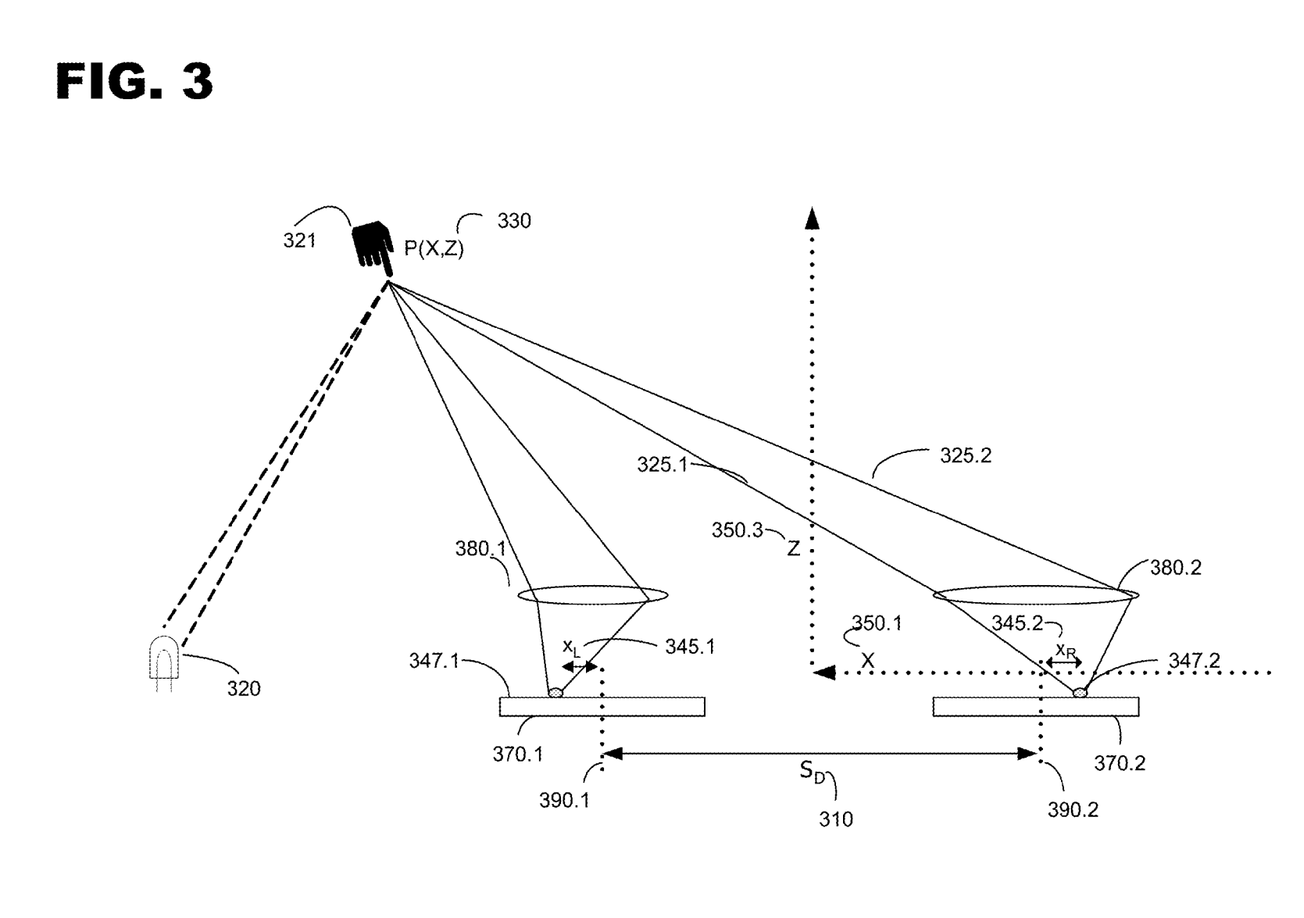
FIG. 3 shows a method for computing the location of an object in an embodiment.

FIG. 3 illustrates the X 350.1 and Z 350.3 plane for computing the location 330 of an object 321 based on light from a light source 320 reflected by the object 321. In an embodiment, a light source 320 emits light reflected by an object 321 that is focused by optics 380 to form spots 347.1, 347.2 on the PSDs 370. The two PSDs 370 are connected to electronics (not illustrated) which may include one or more operational amplifiers and differencing and summing instrumentation amplifier configurations to measure the location of the spots 347.1, 347.2. $S_D$ 310 is the distance between the two PSDs 370. In an embodiment, the location of the spots 347.1, 347.2 may be measured relative to the center of the PSDs 390 as $x_L$ 345.1 and $x_R$ 345.2.

In an embodiment, the electronics measures the centroid of the intensity distribution of the reflected light on the surface of the PSDs 370. As described herein, the electronics may calculate the position of multiple light sources using time or frequency modulation. If f is the focal length of the aperture 380, which may be a slit in a housing, then for each of the PSDs 370 the electronics (not illustrated) may calculate the location of the imaging spot using the following equations:

$$x_L = \frac{f}{Z}\left(X + \frac{S_D}{2}\right)$$

$$x_R = \frac{f}{Z}\left(X - \frac{S_D}{2}\right)$$

Where $x_L$ is 345.1, $x_R$ is 345.2, Z is 350.3, and $S_D$ is 310. After performing the above calculations, the electronics may calculate X 350.1 from the following equation:

$$X = \left(\frac{S_D}{2}\right)\left(\frac{x_L - x_R}{x_L + x_R}\right)$$

Where $x_L$ is 345.1, $x_R$ is 345.2, X is 350.1, and $S_D$ is 310. Having determined lateral position, the electronics may calculate the X 350.1 and Z 350.3 from both the outputs of the PSDs as:

$$Z = \frac{f}{x_L - x_R}S_D$$

Where $x_L$ is 345.1, $x_R$ is 345.2, Z is 350.3, and $S_D$ is 310.

Referring back to FIG. 1, if one or more of the PSDs 270 are two-dimensional, then the electronics may calculate the Y 175.2 location directly by:

$$Y = \frac{Zy_L}{f} = \frac{Zy_R}{f} = \left(\frac{Z}{f}\right)\left(\frac{y_L + y_R}{2}\right)$$

Where Y is 175.2, $y_L$ is 190.4, $y_R$ is 190.6, and Z is 175.3. From the above equations, the electronics may calculate the location of point source of light 130 by using the electrical signals generated by a pair of PSDs 170 in response to the incident light from the light source.

In an embodiment, the electronics may adjust the calculated location 330 of the light source using correcting calculations that compensate for distortions of the aperture 380. For example, the aperture 380 may distort the position 347 of the centroid on the surface of the PSD 370 due to effects such as pincushion, astigmatism, and other sources of error. In an embodiment, the electronics may adjust the calculated location 330 of the light source based on distortions caused by the design of the PSD 370. The electronics may be calibrated to tweak the calculated adjustments to the location 330 of the light source.

Role of Light Source and Light Detector May Be Reversed

Figure 4:
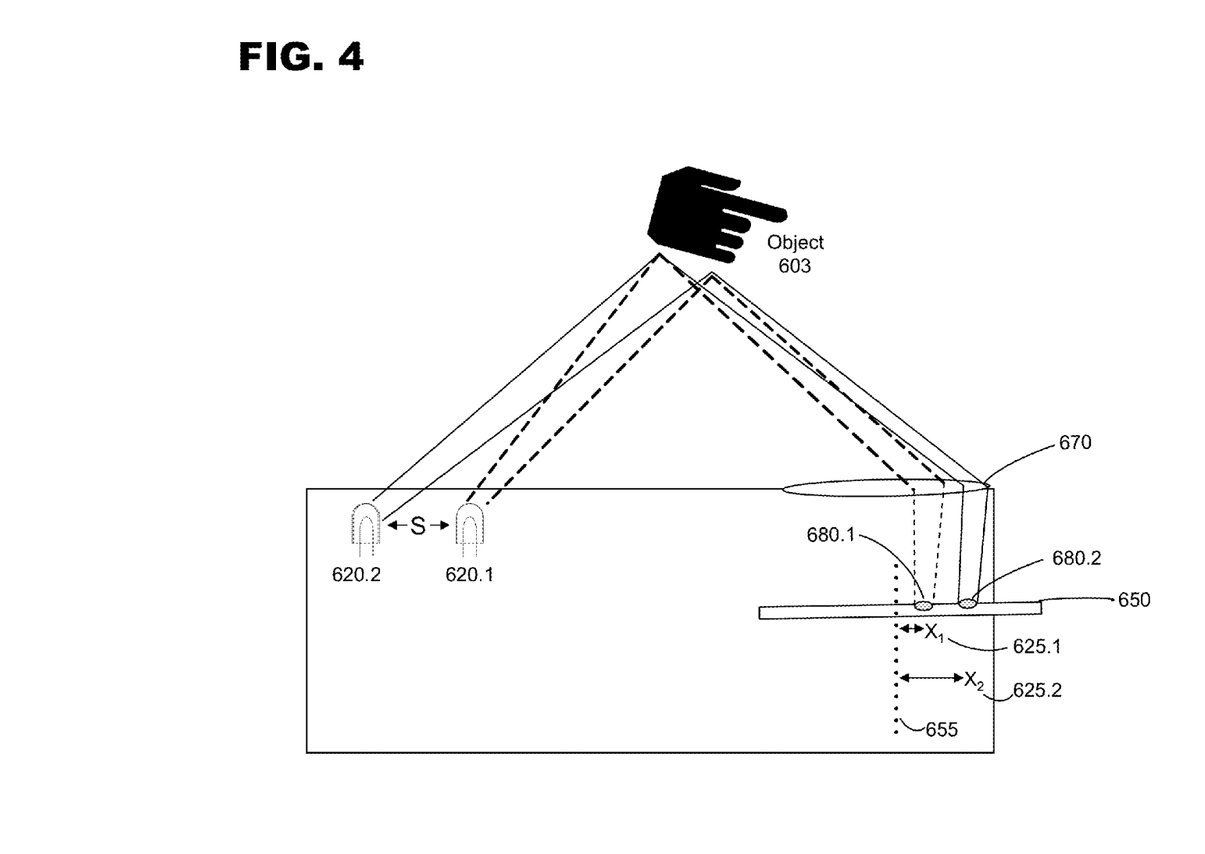
FIG. 4 shows an embodiment with two light sources emitting modulated light reflected into a light detector.

FIG. 4 illustrates an embodiment of the present invention with two light sources 620 emitting modulated light and a light detector 650. Each of the two or more light sources 620 may emit light of a different wavelength that is reflected by an object 603 and detected by the light detector 650 to calculate the position P(X,Y,Z) of the object 603 and/or the intensity of light reflected by the object. As illustrated below, the roles of the light detectors 650 and the light sources 620 may be interchangeable.

Two light sources 620 can be used at a fixed separation S with a single light detector 650 that is part of a single device, such a portable computing device. The two light sources 620.1 and 620.2 may form two spots on the light detector 650 because of the aperture 670. The electronics may distinguish between the two light sources of different wavelengths 620 using methods and apparatuses disclosed herein. The electronics may calculate the X and Y coordinates. The basic idea of calculating distances remains the same and is done by triangulation. In triangulation, two separate triangles are imagined linking rays emerging from the each of the LEDs, reflecting off of the object, and forming two images (one from each LED) whose centroids are measured. From knowing the distance between LEDs and the detector, as well as the parameters of the lens, the X, Y, and Z coordinates may be calculated. The average X and Y coordinates are still given by similar equations as earlier:

$$X = \frac{x_1 + x_2}{2}$$

$$Y = \frac{y_1 + y_2}{2}$$

Where, $x_1$ 625.1 and $x_2$ 625.2 are the position of the two reflected spots 680 from the center 655 of the light detector 650.

The Y coordinate may be calculated with data from either a two-dimensional light detector 650 or a second light detector (not illustrated). The second light detector may be oriented differently than the light detector 650 and may be oriented along the y-axis. The Z coordinate may be measured from the solution of two triangles. The two triangle solution may also be used in an embodiment where the detector is in the center, the two LEDs flank the detector on either side, and the LEDs are separated by distance S, which may be the exact compliment of the earlier case. The electronics may calculate the proximity of the object to the detector using stored values of the separation S of the light sources 620 and stored values of the focal length f of the aperture 670. The electronics may then calculate Z by using the following equation:

$$Z = \frac{f}{(x_2 - x_1)} S$$

Where $x_1$ 625.1 and $x_2$ 625.2 are the position of the two reflected spots 680.1, 680.2. For different geometry, such as shown in FIG. 4, one can derive the appropriate equations using measured centroids and simple trigonometry.

Figure 5:
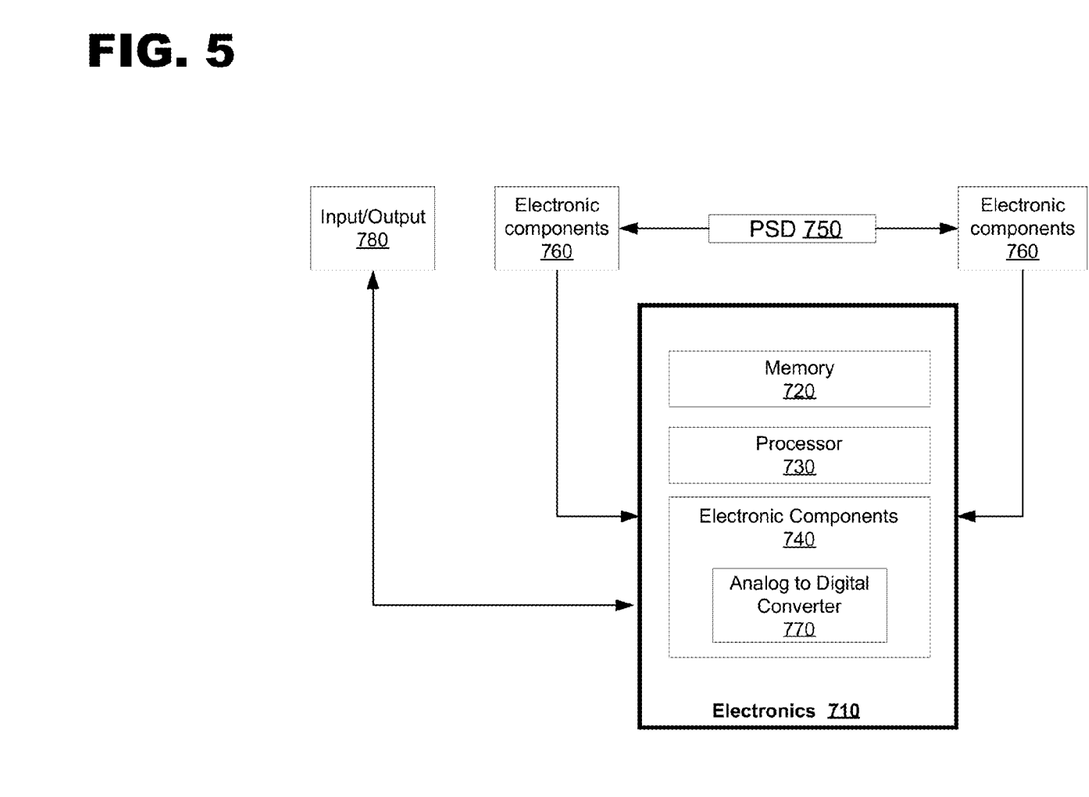
FIG. 5 shows the configuration of electronics of an embodiment.

FIG. 5 illustrates an embodiment for the electronics 710. The electronics 710 may include one or more memories 720, one or more processors 730, and electronic components 740. The electronics 710 may communicate with other components through an input/output interface 760, which may include amplifiers connected to the sensor 750 that amplify photocurrents and prepare them for conversions by an analog to digital converter 770. The electronics 710 may be communicatively coupled to one or more optical detectors 750 or PSDs (as illustrated) 750 or the electronics 710 may be communicatively coupled to electronic components 760, and the electronic components 760 may be directly communicatively coupled to the one or more PSDs 750. The electronics 710 may calculate the position of the movable object and/or the reflected light intensity by receiving data collected from the optical detectors 750. The data may be processed by the electronic components 760 outside the electronics 710 before being received by the electronics 710. The electronics 710 may include an analog to digital converter 770 for converting the analog data from the PSDs 750 and/or the electronic components 760 to digital data for processing by the processor 730. The memory 720 may be RAM and/or ROM and/or any type of memory able to store and retrieve instructions and may include program instructions for determining the position and/or rotation of one or more movable devices. The processor 730 may be a computer processor, central processing unit (CPU), or other type of processing device.

Multiple controllers 710 may be used to determine the position of the movable device. The electronics 710 may perform only part of the calculating necessary to determine the position of the movable device. The electronic components 740 and 760 may include operational amplifiers; amplifiers; differencing and summing instrumentation amplifier configurations to measure the location of the spot of light; analog to digital converters; a pair of current detectors, each coupled to the PSD edges, or two pair of current detectors for a two-dimensional light detectors; wires for connecting the current detectors to the other electronic components; a pair of differential amplifiers to compare the left-edge and right-edge currents from each light detector; and/or other electronic or electrical circuitry for implementing the functionality of the present invention. The electronic components may be positioned or grouped in many ways as along as photocurrents may still be measured. For example, there may be one amplifier per output of the light detector, the light detectors may share a common set of amplifiers, there may be no differential amplifier, or there may be one or more differential amplifiers as part of the controller. Positional information for the movable device may be computed entirely by one device or the computations may be divided among two or more devices.

The electronics 710 may include a single digital signal processing engine that can separate and track multiple light sources. The electronics 710 may receive data from PSDs 750 collected at a remote device and communicated to the electronics 710. For example, a remote game controller containing PSDs 750 may communicate data from the PSDs 750 wirelessly to the electronics 710 for the electronics 710 to calculate the position or rotation of the remote controller. The electronics 710 may be communicatively coupled to many optical detectors or PSDs 750 and/or light sources. The electronics 710 may be configured to modulate a light source either in time or frequency so that the light source may be distinguished from other light sources. The electronics 710 may be configured to calculate the rotation of an object based on the spectrum of light received from multiple light sources.

In an embodiment, the light detectors may be PSDs and the PSDs may be linear light detectors that provide lateral currents at each end (left-edge ($I_L$) and right-edge ($I_R$) currents) that vary depending on the location of incident light on the PSD's surface. In another embodiment, the PSDs may be two dimensional. There may be four currents provided at each end of the PSDs (left-edge ($I_L$), right-edge ($I_R$), back-end ($I_B$), and front-edge ($I_F$) currents) that vary depending on the location of incident light on the PSD's surface. The light detectors may include other embodiments.

In an embodiment, optics provided in a common housing with the light detectors may focus light from the light sources into a spot on the light detector surface. The imaging optic or optics may be a pin hole, a slit, a fish eye lens, or any type of lens or device that tends to focus the light on the PSD. Positional information may be determined by determining the centroid of the focused light or spot on the PSD surface and by using the focal properties of the imaging optics.

Additional light sources and/or detectors may be used to increase the accuracy of locating the movable object, increase the area of sensitivity, decrease the possible of the light detectors and/or sources from being obstructed, or increase the accuracy of the reflected light intensity measurement. The light sources and detectors may be time or frequency modulated to differentiate between light sources.

Figure 6:
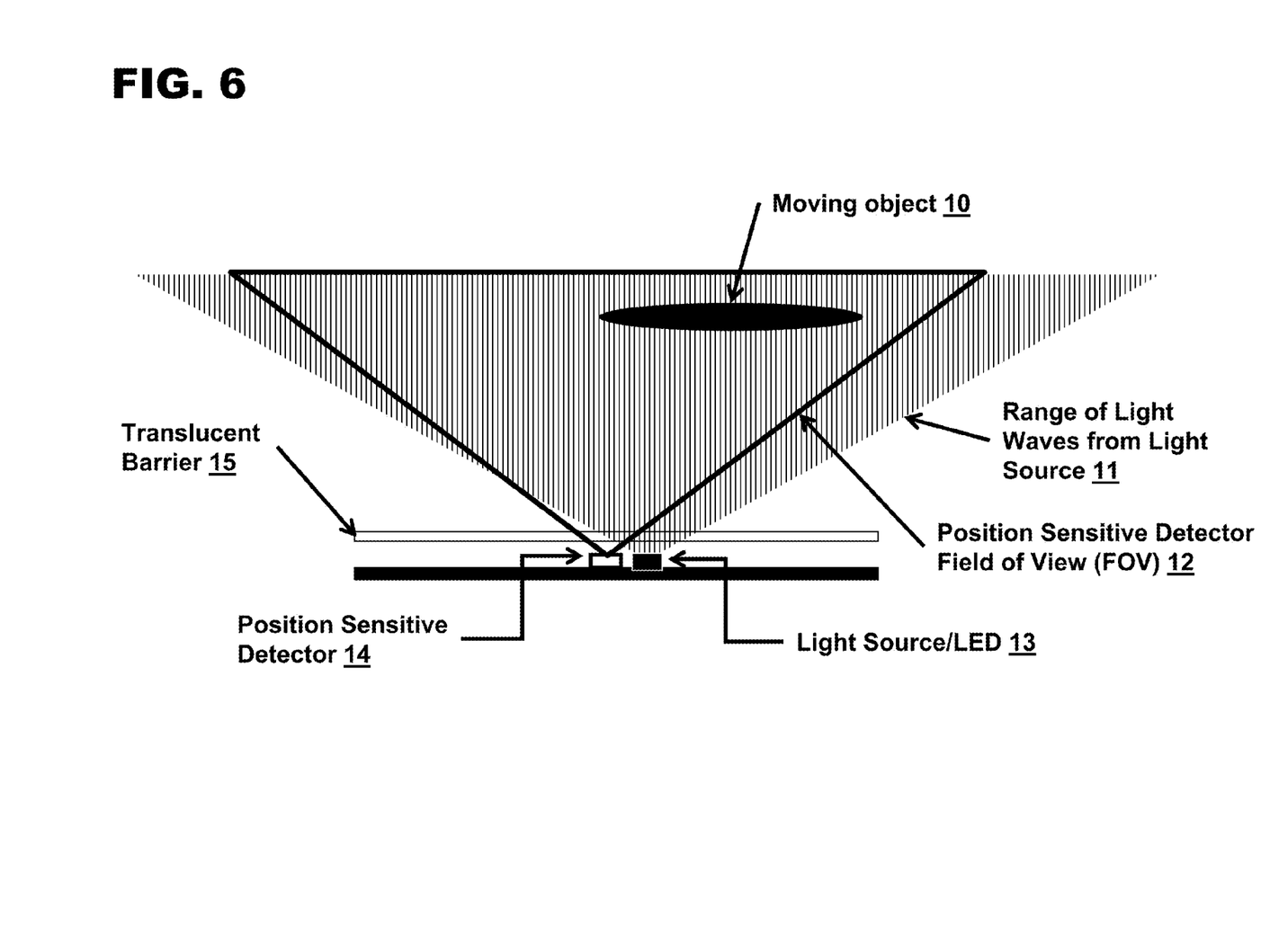
FIG. 6 shows an exemplary configuration of a light source and detector in relation to a moving object.

FIG. 6 shows an exemplary configuration of a light source 13 and detector 14 in relation to a moving object 10. In this embodiment, the position of a moving object 10 may be tracked and calculated using light emitted from the light source/LED 13 that is reflected off the moving object 10 and detected at the position sensitive detector 14 when the moving object is in the field of view of the detector. The striped triangular region 11 shows an exemplary range of the electromagnetic waves emitted from light source 13, whereas the solid lined triangular region 12 shows an exemplary field of view of the position sensitive detector 14. In an embodiment, a transparent barrier 15 may be positioned between the object 10 and the light source 13 and detector 14. The light source 13 and/or detector 14 may also include imaging optics to improve accuracy. The imaging optics may be used to focus the range of light emitted from the light source 13, focus the field of view of the detector 14, or both.

In an embodiment, the light 11 from the light source/LED 13 may be modulated at a high frequency of several kHz, MHz, or more and the position sensitive detector 14 and its associated electronics may be synchronized to the modulated light source. In an embodiment, synchronizing the modulation of the detector 14 and the light source 13 in the time or frequency domain may result in the rejection of other forms of electromagnetic radiation such as ambient lighting, which generally may have frequency variations in the sub-kHz domain. Modulation may also be used to "decode" and differentiate the signals from multiple light sources, each of whose reflection can be tracked independently.

In an embodiment, position information of an object 10 may be calculated at different rates. Calculating position information of the object 10 at frequencies of hundreds or even thousands of Hertz may further increase positioning accuracy and enable tracking of object 10 moving at high speeds while reducing delay, such as additional frame processing time, associated with pixilated imaging-based movement detection technology.

Aside from calculating position information of a moving object 10 located above the transparent barrier 15 and within the field of view of the position sensitive detector 14, a change in position and pressure applied along the surface of the transparent barrier 15 may also be tracked and calculated. A change in pressure applied to the surface of the transparent barrier may be detected when relatively elastic objects 10, such as fingers, are used and at least one of the light sources is passed through the barrier. When additional pressure is placed on the surface of the transparent barrier by a relatively elastic object, the elastic object may further deform from its original shape to cover an additional surface area of transparent barrier 15 resulting in additional light being reflected from the light source into the detector.

In some embodiments multiple sources of electromagnetic radiation may be used. The electromagnetic waves emitted from each of the light sources may be uniquely modulated in the time or frequency domain in order to identify and distinguish the originating light source of reflected waves measured at the detector.

Figure 7:
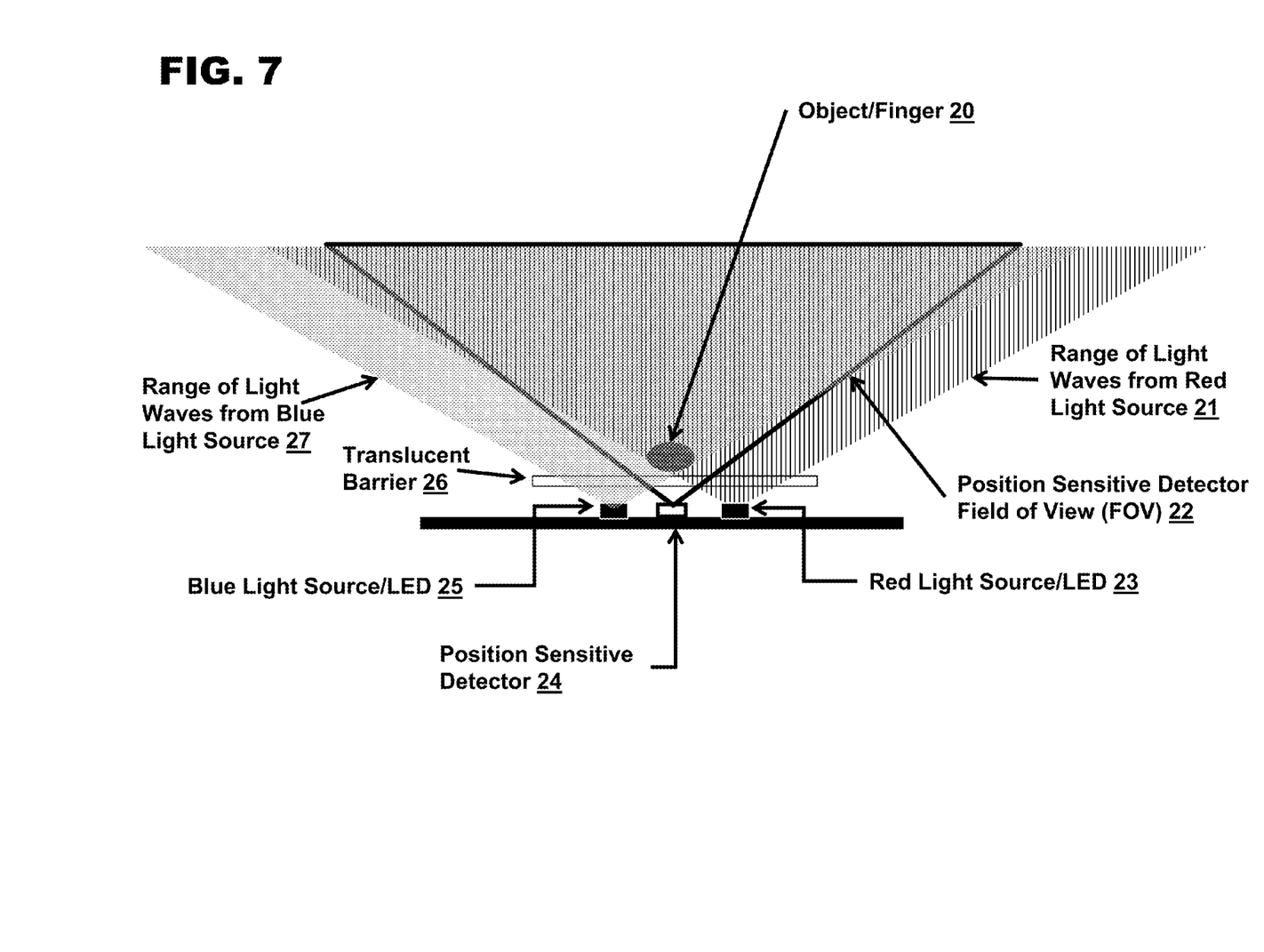
FIG. 7 shows an embodiment with two light sources emitting light at possibly different wavelengths and may be modulated so as to be uniquely identified.

FIG. 7 shows an embodiment with two sources 23 and 25 emitting electromagnetic radiation at different frequencies. The vertically striped triangular region 21 shows an exemplary range of red light waves emitted from light source 23, while the horizontally striped triangular region 27 shows an exemplary range of blue light waves emitted from light source 25. The horizontally and vertically criss-crossed region shows the overlapping range of red 21 and blue 27 light. The solid line triangular region 22 shows the field of view of detector 24.

In some embodiments, having more than one uniquely modulated light source 23 and 25 may allow calculation of position or movement in three dimensions by triangulating the position of the object based on the detected position of the reflected waves from the multiple light sources at the detector. In an embodiment, a distance between an object 20, and light sources 23 and 25, or other position relative to a light source 23 or 25 or detector 24 may be calculated. This calculation may be based on a triangulated location of the object based on the measured position of the reflected waves at the detector.

Aside from using multiple LEDs encoded either in time domain or frequency domain to enhance spatial information about the object in 3D space, other modulation codes can be applied to LEDs of different colors of light. In that case, spectrometric information about the object can be measured as well as spatial information described previously. A classic example of this is measurement of blood oxygen as in pulse oximetry, where two colors of light are used (there are many choices but wavelengths near 660 nm and 940 nm are often selected) to perform spectrometry on the blood inside the body. The PPG at each of the wavelengths may be measured independently. The technique can be extended to many colors of light. In some applications, the selected wavelength of the light sources may result in more accurate measurements. For example, two or more light sources may be used to measure blood oxygen levels, with each light source (at different wavelength) producing independent PPG signals.

Figure 10:
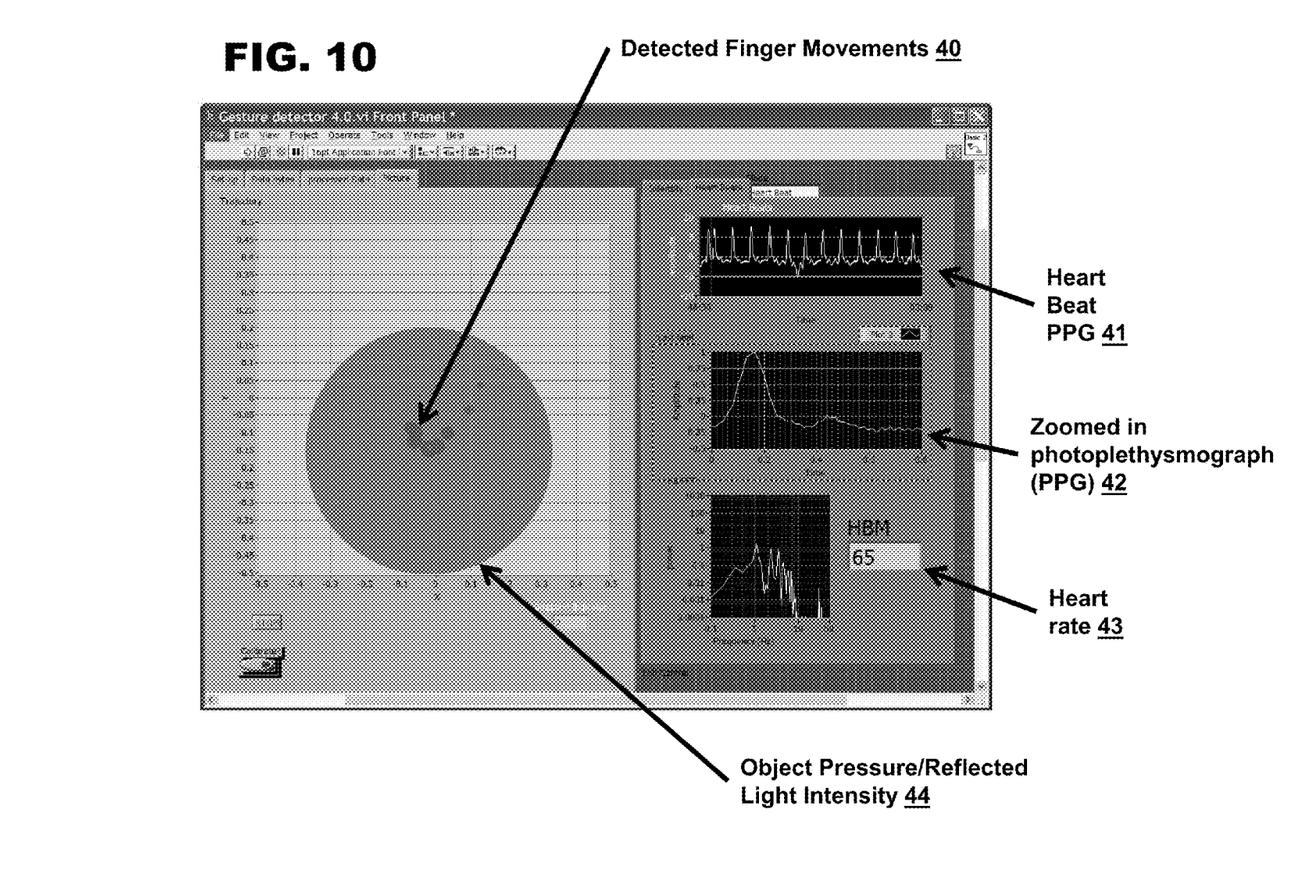
FIG. 10 shows exemplary data that may be measured in an embodiment.

The PPG signals for pulse oximetry may be calculated from the measured PPG signals at each of the wavelengths. (see, for example, FIG. 10). The PPG signals may be measured by calculating the DC signal level and the AC amplitude at wavelengths $\lambda_1$ and $\lambda_2$. The ratio:

$$R = \frac{(I_{AC}/I_{DC})_{\lambda_1}}{(I_{AC}/I_{DC})_{\lambda_2}}$$

is a measure of the saturated blood oxygen. The connection between R and the actual blood oxygen may be based on simple physical theory or an empirically measured fit between R and blood oxygen levels. This medical information may be provided in an embodiment in conjunction with object tracking functionality.

Figure 8:
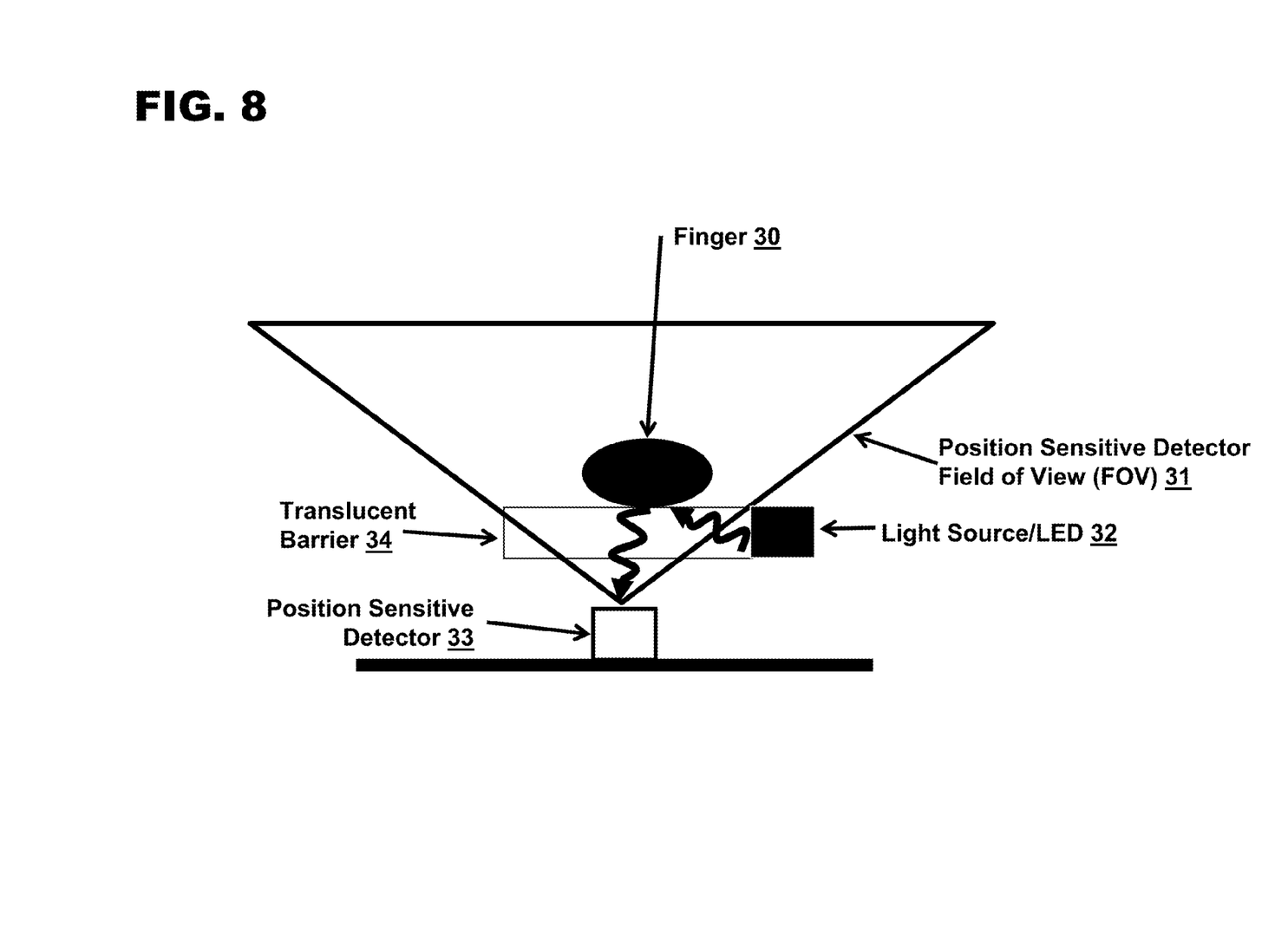
FIG. 8 shows another exemplary configuration where a light source may be positioned to emit light waves into a transparent barrier.

FIG. 8 shows another exemplary configuration where a light source 32 may be positioned to emit light waves into the transparent barrier 34. When an object, such as a finger 30, touches the surface of the transparent barrier 34 within the field of view 31 of detector 33, the light waves from the light source 32 may be reflected from the barrier 34 into the detector 33. In an embodiment, the relative opacity and surface area of the object covering the transparent barrier 34 may directly affect the amount of light from the light source 32 that is reflected into the detector 33. In an embodiment, the amount of light from the light source 32 reflected into the detector 33 may only vary if an object comes into contact with some portion of the surface area of the transparent barrier 34. In such an embodiment, the amount of light from the light source 32 reflected into the detector 33 may not change if an object does not come into direct contact with the surface of the transparent barrier 34 even if the field of view 31 of the detector 33 extends beyond the surface of the transparent barrier 34.

Also, elastic objects such as a finger will scatter more light as the object is pressed against the barrier and the surface area of the object in contact with the barrier increases. This may be used as a proxy for the pressure and used to create the effect of pressure sensing, which may be used in both creating rich user interfaces (pressure may be used for zooming, highlighting, drawing effects).

Another important aspect of measurement of pressure may be related to the measurements of PPGs. For example, if PPGs are measured at the finger tip, then the heart beat signal vanishes as the finger is pressed against the barrier. The change in the shape of PPG vs. pressure may be used to deduce blood pressure.

Since motion may be tracked while measuring PPG, the motion information may be used to improve the PPG readings by reducing erroneous readings in the light intensity measured by the detector due to the motion. When measuring changes in total light intensity over time, changes in total intensity due to lateral motion of the finger may be accounted for in the calculated intensity to more accurately measure the intrinsic changes to the total intensity. In an embodiment, movement effects may be accounted for by either correcting the measurement data or rejecting measurement data during motion.

Traditionally, PPG's have only measured total intensity and not changes in the thickness or position of a pulsating artery as the PPG is measured. In an embodiment, both the changes in thickness and position of a pulsating artery may be measured. These measurements may provide additional clinical information on arterial compliance, which may be correlated to PPG measurements.

Figure 9:
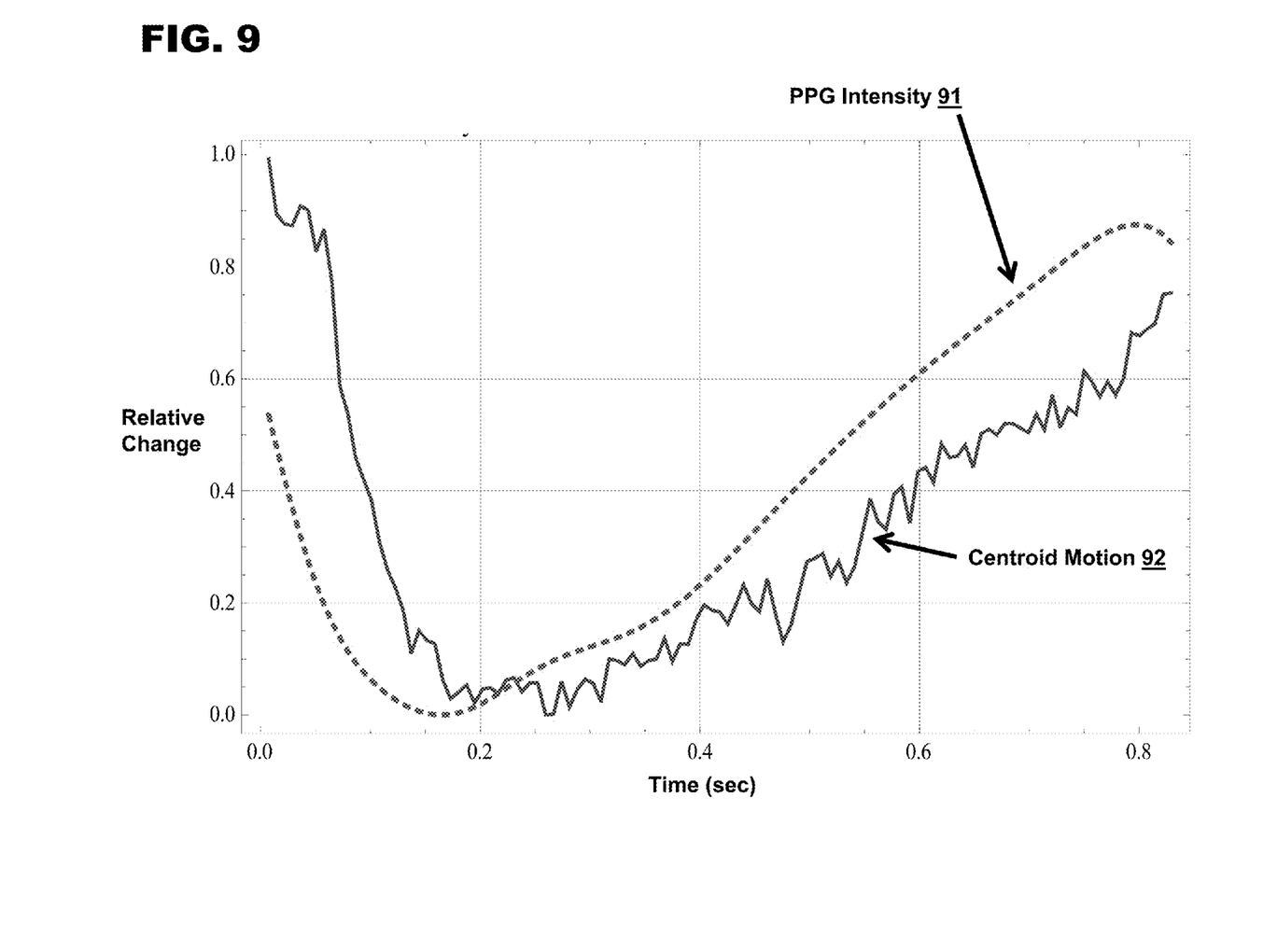
FIG. 9 shows an exemplary graph of the relative change of PPG intensity and centroid motion over time.

FIG. 9 shows a graph of the relative change over time in one heart beat period of the PPG intensity and the motion of the centroid of the PPG on the barrier. The dashed line shows the relative change over time of the measured PPG light intensity 91. The solid line shows the relative change over time of the motion of the detected centroid 92 of the PPG measurements on the barrier. The relative change of unity in the graph in position of the centroid is approximately 1 μm.

In some embodiments, multiple light sources, each tagged with unique modulation code in frequency or time domain, may be used. Some of the light sources may emit light into a volume of space, as shown in FIGS. 6 and 7, while others may emit light that may be confined to the transparent barrier as shown in FIG. 8. The light sources emit light into the volume of space may be used to measure data of objects above the surface of the barrier, while those that emit light into the transparent barrier may be used to measure data of objects touching the surface of the barrier.

In an embodiment, when a finger or other body part proximate to flowing blood is held relative still in an area within the field of view of a position sensitive detector having a high dynamic range, certain medical information including heart rate and optical heart waveforms, also known as photoplethysmograph (PPG), may be calculated from the intensity of the reflected light measured at the detector. In an embodiment, a high dynamic range may exceed 50 dB and may be configured to be between 80 and 100 dB, though other ranges may also be used in other embodiments. Other medical information, such as blood oxygen information may be calculated in a embodiment through a pulse oximetry type technique by comparing measured intensities of reflected light at the detector from two light sources having different wavelengths. Other medical information that may be obtained from reflected electromagnetic radiation may also be calculated. In an embodiment, one of the light sources may have a wavelength around 660 nm while the other light source may have a wavelength around 900 nm, though in other embodiments different wavelengths may be used. For example, using three or more colors may result in improved measurement of blood oxygen or other blood chemicals depending on the selected wavelengths.

Embodiments of the invention may be used to track hundreds of light sources (each at different wavelengths, if necessary) simultaneously. In an embodiment, recording PPG data at various finger or other body part pressures against the barrier may provide a data set that may be used for measurement of blood pressure or for providing feedback to the user to apply optimal pressure for best readings. A graphical user interface may be used to provide feedback to the user to adjust the position or pressure of the finger or body part on the transparent barrier to improve the accuracy of results.

FIG. 10 shows exemplary data that may measured in an embodiment. The right side of FIG. 10 shows an exemplary heartbeat photoplethysmograph (PPG) 41, a magnified PPG 42, and a calculated heart rate 43 of an individual placing a finger on the surface of an exemplary transparent barrier. The left side of FIG. 10 shows the detected movements 40 of the individual's finger on the transparent barrier as well as the intensity of the light 44 from the light source that was reflected by the user's finger into the detector.

Different combinations of the above features and functions may be combined in different devices using a single set of light sources and detectors. Thus, in a device is it possible to use one light source and one light detector or one pair of light sources and one pair of light detectors to perform one or more of the following functions: locating the position of an object; tracking movement of an object; measuring a distance to an object; calculating a change in pressure applied to a surface; determining an individual's heart rate; calculating an individual's optical heart waveform or photoplethysmograph; and calculating an individuals blood oxygen content through pulse oximetry. Accordingly, embodiments of the invention may be incorporated into devices where such functionality is desired.

In an embodiment, a position sensitive detector for measuring PPG may provide feedback to a user to assist the user in placing a body part at an optimal location relative to the sensor. An ordinary photodetector would not be able to provide such feedback. Additionally, in an embodiment, simultaneous tracking of finger pressure and PPG may allow one to deduce blood pressure with some calibration in an embodiment.

Embodiments of the invention may be included device such as cell phones, navigation equipment, laptops, computers, remote controllers, computer navigation devices, electronic devices, televisions, video players, cameras, watches, portable devices, telephones, and any other device. Embodiments of the invention may be used in portable devices where space is at a premium; since the same circuitry may be used to perform multiple functions, redundant systems may be eliminated thereby saving space. For example, the position location and/or movement tracking features maybe combined with the medical information functionality, such as heart rate, optimum heart waveform, and/or blood oxygen content measurements to assist a user in repositioning a finger or other body part to obtain optimum results. Other combinations of different features and functionality previously mentioned may also be implemented in other embodiments.

We claim:

1. A device comprising:
a source emitting electromagnetic radiation through a transparent barrier;
a position sensitive detector behind a first side of the barrier measuring a position and intensity of the electromagnetic radiation reflected off a body part of an organism placed on a surface of a second side of the barrier, the source modulated to reduce an effect of ambient radiation on the measurement; and
electronics to calculate (a) a position of the body part on the surface of the barrier based on the position of the measured reflected radiation and (b) a photoplethysmograph from changes to the reflected light intensity;
wherein the position sensitive detector measures the position of the reflected electromagnetic radiation by generating first and second currents at first and second ends, respectively, of the position sensitive detector, the first and second currents varying depending on a light distribution of the reflected electromagnetic radiation on a surface of the position sensitive detector facing the first side of the barrier.

2. The device of claim 1, wherein the calculated position of the body part updates as the body part is moved.

3. The device of claim 1, wherein the electronics further calculate a heart rate of the organism from the photoplethysmograph.

4. The device of claim 3, wherein the electronics are configured to instruct a user where to move the body part to improve the reflected light intensity.

5. The device of claim 1, further comprising a plurality of sources, each emitting electromagnetic radiation having a unique wavelength, the sources modulated to identify the source of reflected radiation at the detector.

6. The device of claim 5, wherein the wavelength of the radiation from a first source is around 660 nm and the wavelength of the radiation from a second source is around 900 nm.

7. The device of claim 5, wherein the electronics further calculate a measure of oxygenation.

8. The device of claim 1, wherein the device is a computing device.

9. The device of claim 8, wherein the computing device is portable.

10. The device of claim 9, wherein the computing device is a personal digital assistant.

11. The device of claim 1, wherein the electronics determine that higher levels of scattered light correspond to greater pressure applied by the body part.

12. The device of claim 11, further comprising a user interface, and wherein at least one of: a degree of zooming and highlighting performed on the user interface, indicates a level of pressure exerted on the user interface.

13. The device of claim 1, wherein the source emits the electromagnetic radiation in at least two different wavelengths, and the electronics calculate the photoplethysmograph for each one of the different wavelengths.

14. The device of claim 1, wherein the barrier includes one of a focusing lens and an aperture.

15. The device of claim 14, wherein one of a focusing lens and an aperture is located in the barrier and adjacent to the surface on the second side of the barrier.

16. The device of claim 1, wherein one of a focusing lens and an aperture is located between the barrier and the position sensitive detector on the first side of the barrier.

17. The device of claim 1, wherein the electronics further calculate one of a heart rate and a blood oxygen content.

18. The device of claim 1, wherein the position sensitive detector measures the position of the reflected electromagnetic radiation by generating, in addition to the first and second currents, a third current and a fourth current at third and fourth ends, respectively, of the position sensitive detector, the third and fourth currents varying depending on a light distribution of the reflected electromagnetic radiation on a surface of the position sensitive detector facing the first side of the barrier.

19. A method comprising:
emitting electromagnetic radiation from a source through a transparent barrier;
reflecting the emitted radiation off a body part of an organism placed on a surface of a first side of the barrier;
detecting a position and intensity of the reflected radiation at a position sensitive detector behind a second side of the barrier;
modulating the radiation to reduce an effect of ambient radiation on the detection;
calculating a position of the body part on the surface from the detected position of the reflected radiation; and
calculating a photoplethysmograph from changes to the reflected radiation intensity;
wherein the position sensitive detector measures the position of the reflected electromagnetic radiation by generating first and second currents at first and second ends, respectively, of the position sensitive detector, the first and second currents varying depending on a light distribution of the reflected electromagnetic radiation on a surface of the position sensitive detector facing the first side of the barrier.

20. The method of claim 19, further comprising:
emitting electromagnetic radiation from a plurality of sources having unique wavelengths through the transparent barrier, the sources modulated to identify the sources of reflected radiation at the detector;
comparing the reflected radiation intensities from each source; and
calculating a measure of oxygenation from the comparison.

21. The method of claim 20, wherein the modulation of the sources includes modulation in one of a frequency domain and a time domain.

22. The method of claim 19, further comprising focusing, by one of a focusing lens and an aperture, the reflected radiation on the position sensitive detector.

23. The method of claim 19, further comprising calculating one of a heart rate and a blood oxygen content from changes to the reflected radiation intensity.

24. A device comprising:
means for emitting electromagnetic radiation through a transparent barrier;
means for measuring, from behind a first side of the barrier, a position and intensity of the electromagnetic radiation reflected off a body part of an organism placed on a surface of a second side of the barrier; and
means for calculating (a) a position of the body part on the surface of the barrier based on the position of the measured reflected radiation and (b) a photoplethysmograph from changes to the reflected light intensity;
wherein the means for measuring the position of the reflected electromagnetic radiation includes a step for generating first and second currents, the first and second currents varying depending on a light distribution of the reflected electromagnetic radiation on a surface of means for measuring the position of the reflected electromagnetic radiation facing the first side of the barrier, and
wherein the means for emitting electromagnetic radiation through a transparent barrier further includes means for modulating to reduce an effect of ambient radiation on the measurement.

25. The device of claim 24, wherein the means for calculating updates the calculation as the body part is moved.

26. The device of claim 24, wherein the means for calculating further calculates a heart rate of the organism from the photoplethysmograph.

27. The device of claim 24, wherein the means for emitting electromagnetic radiation emits a plurality of wavelengths of electromagnetic radiation, each having a unique wavelength.

28. The device of claim 27, wherein the means for emitting electromagnetic radiation emits one of the plurality of wavelengths of electromagnetic radiation.

29. The device of claim 27, wherein the means for emitting electromagnetic radiation modulates the plurality of wavelengths of electromagnetic radiation to identify a source of reflected radiation at the detector.

30. The device of claim 24, wherein a wavelength of the electromagnetic radiation emitted from the means for emitting electromagnetic radiation is around 660 nm or around 900 nm.

31. The device of claim 24, wherein the means for calculating further calculates a measure of oxygenation.

32. The device of claim 24, wherein the means for calculating is configured to instruct a user where to move the body part to improve the reflected light intensity.

33. The device of claim 24, wherein the device is a computing device.

34. The device of claim 33, wherein the computing device is portable.

35. The device of claim 34, wherein the computing device is a personal digital assistant.

36. The device of claim 24, wherein the means for calculating determines that higher levels of scattered light correspond to greater pressure applied by the body part.

37. The device of claim 36, the device further comprising means for interfacing with the device, and wherein at least one of: a degree of zooming and highlighting performed on the means for interfacing with the device, indicates a level of pressure exerted by the body part.

38. The device of claim 24, further comprising means for calculating one of a heart rate and a blood oxygen content from changes to the reflected radiation intensity.

39. The device of claim 24, further comprising means for focusing the reflected radiation on the means for measuring the position of the reflected electromagnetic radiation.

40. The device of claim 24, wherein the means for measuring the position of the reflected electromagnetic radiation includes means for generating, in addition to the first and second currents, a third current and a fourth current, the third and fourth currents varying depending on a light distribution of the reflected electromagnetic radiation on a surface of the means for measuring the position of the reflected electromagnetic radiation facing the first side of the barrier.

* * * * *